United States Patent

Biagi

[11] Patent Number: 5,705,134
[45] Date of Patent: Jan. 6, 1998

[54] SCISSOR DISINFECTING DEVICE

[76] Inventor: Matthew P. Biagi, 415 Higgins St., Humble, Tex. 77338

[21] Appl. No.: 640,560

[22] Filed: May 1, 1996

[51] Int. Cl.⁶ .................... A61L 2/18; B65D 1/34
[52] U.S. Cl. ........................... 422/300; 422/310
[58] Field of Search .................. 422/102, 104, 422/300, 310; D24/227

[56] References Cited

U.S. PATENT DOCUMENTS

| 4,389,374 | 6/1983 | Sutton et al. | 422/104 |
| 4,407,958 | 10/1983 | DeGraff, Jr. | 422/104 |
| 4,973,315 | 11/1990 | Sincock | D24/227 |
| 4,978,510 | 12/1990 | Smith | 422/310 |
| 5,128,105 | 7/1992 | Berthold et al. | 422/104 |
| 5,133,939 | 7/1992 | Mahe | 422/300 |

OTHER PUBLICATIONS

The Fisher Scientific Catalog, pp. 243,1042,1043,1045–1048 (1988).

*Primary Examiner*—Cynthia L. Nessler

[57] ABSTRACT

A single one-piece plastic panel that is bent to form a bottom, side, and top of a device. The bottom will act as a means of supporting the device. The side will act as a means of supporting the top and joining the top and bottom portions of the panels. The top portion of the panel will have a plurality of holes in which a tube can be inserted in each hole. The tube will have a sealed bottom to hold a disinfecting solution to sanitize scissors. The design of the tube may have a lip to easily grab and remove the tube from the base of the device. Another alternative design of the tube, may include a tube with a screw top cap so that the solution could be covered when not in use.

1 Claim, 1 Drawing Sheet

SCISSOR DISINFECTING DEVICE

BACKGROUND-FIELD OF INVENTION

This invention relates to a device used to hold scissors so that each scissor can be individually disinfected.

BACKGROUND-DESCRIPTION OF PRIOR ART

In the professional beauty industry, a hair cutting stylist, or hairdresser, will often use hair cutting scissors. Many health regulations now require that scissors in the salon be sanitized after each haircut. A device, U.S. Pat. No. 4,978,510 was invented that is often referred to as a Disinfecting Tray. This device is useful for disinfecting a wide variety of implements that are used in the salon. However, this device is very impractical for scissors. Hair styling scissors are often very expensive, costing in excess of $100, extremely sharp, and normally are stored individually for protection from the razor sharp edges, and to insure that the razor sharp edges are not accidentally damaged by hitting a foreign object.

Another popular method of sterilizing salon instruments is the disinfecting jar. This article is primarily used for disinfecting combs and brushes. This device is very impractical for the sterilization of scissors. Metal objects as scissors often require a different type of disinfecting solution than non-metal objects as combs and brushes. The disinfecting jar is not practical for disinfecting scissors since they have no individual protection from each other and the sharp blades may easily open and become damaged.

None of the devices for sterilization are designed for the hair stylist who wants to individually sterilize the blades of scissors, and insure that the blades stay closed during the disinfecting process to ensure that the blades do not become damaged, and the handles remain outside the object of sterilization to ensure that the user can easily grab the handles of the scissors quickly without the scissor handles soaking in the solution.

OBJECTS AND ADVANTAGES

The scissor disinfecting device has many advantages as follows:

a.) Each scissor has a separate tube for disinfecting. This is important to protect the razor sharp blades of the scissors. Scissor blades should always be individually protected for hitting any other object that may dull or nick the blades.

b. Each scissor in the disinfecting tube will be protected from opening during the disinfecting process to insure that the blades will remain safely closed and will not be exposed and accidently cut someone when trying to retrieve the scissor.

c.) The tubes which hold the disinfecting solution are designed to leave the handles of the scissor out of the solution. This will allow the stylist to be able to easily grab the scissor without having to make the effort in pulling up a device or lift up on a device that takes the object out of the solution, as is true of both examples cited in prior art Stylists often work fast and have little time to spend accessing their shears by complicated devices.

d.) The scissor disinfecting device has individual tubes for disinfecting. This is an advantage because the solution for disinfecting may be considered by some stylists to be expensive. Because each scissor has their own tube of solution, no solution is unnecessarily used.

e.) The scissor disinfecting device is small and takes up minimal space. The counter tops of many stylists are often cluttered with various articles from the salon. For a disinfecting device to be practical it should be compact and allow the user to be able to access the scissors quickly and the complete object of disinfection use a minimal amount of counter space.

BRIEF DESCRIPTION OF THE DRAWINGS

FIG. 1 is a top view of the scissor disinfecting device. This figure illustrates the present invention with its association of disinfecting tubes used to hold the disinfecting solution and the association of the scissors is also illustrated. Four small base feet have been placed on the base bottom to hold the base bottom up from the counter surface the invention will be placed on.

DESCRIPTION OF THE PREFERRED DEVICE

Figure 1:
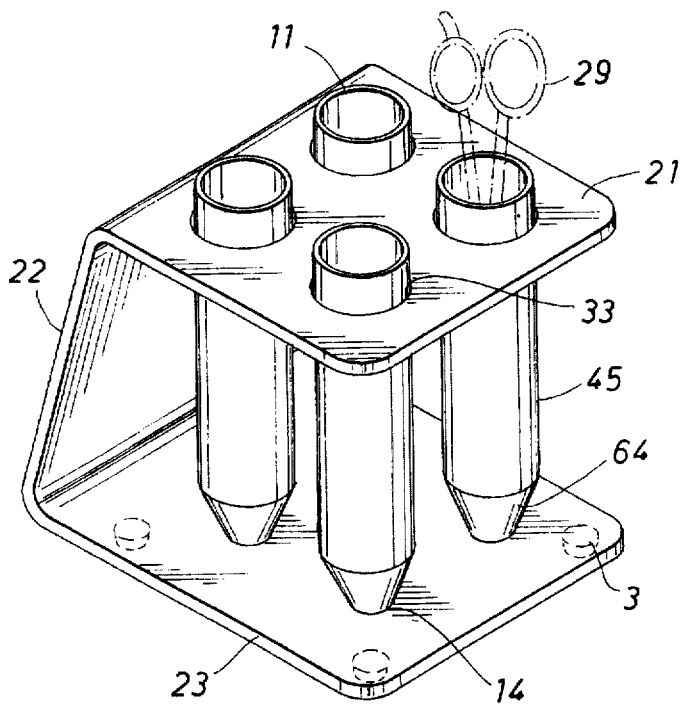
Figure 2:
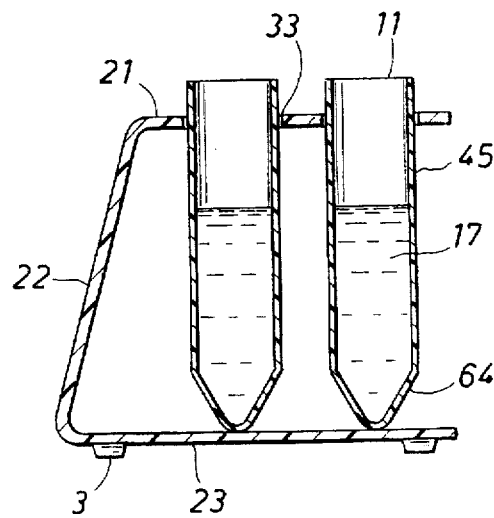
FIG. 2 illustrates a side view of the scissor disinfecting device. The drawing illustrates the present invention showing the tubes to be used to hold the disinfecting solution. Inside each tube the disinfecting solution is illustrated. Two base feet are illustrated on the bottom of the base.
Figure 3:
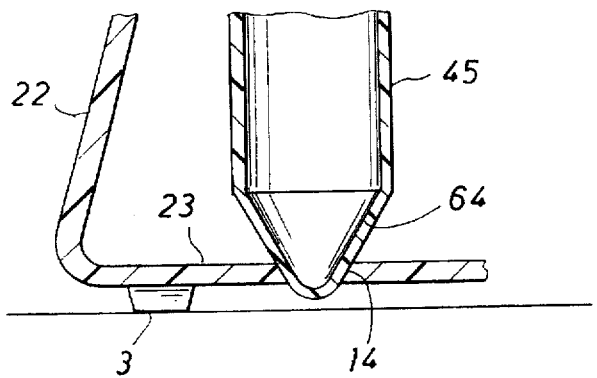
FIG. 3 illustrates a close-up view of an alternative design of the bottom base of the invention. This alternative design shows a hole formed in the bottom of the base to ensure that the disinfesting tubes remain straight in the device.
Figure 4:
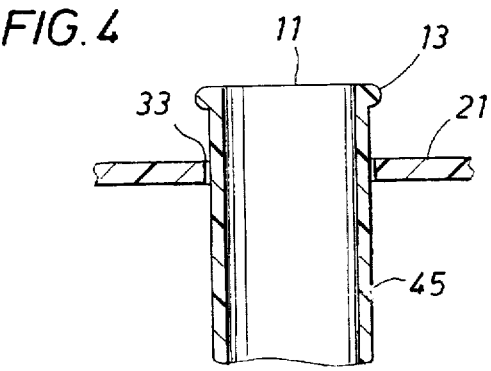
FIG. 4 illustrates a close-up view of an alternative design of the disinfecting tube in association with the top of the base. This drawing illustrates the tube formed with a lip that allows the tube to be easily handled and pulled up out of the base of the device.
Figure 5:
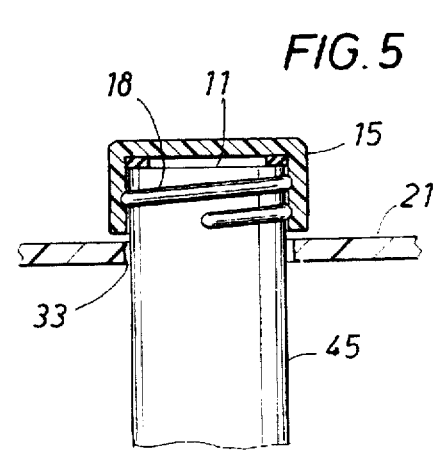
FIG. 5 illustrates a close-up view of an alternative design of the disinfecting tube in the top portion of the base. This drawing illustrates the tube formed with a screw treads and a cap that can be used to cover the disinfecting solution when not in use.

Referring now specifically to the drawings, the top panel (21), side panel (22) and bottom panel (23) of the device is made of plastic with a plurality of holes (33) in the top panel that will hold a disinfecting tube (45) with a sealed bottom end (64) and the top of the disinfecting tube (11) will be open so as to allow scissors (29) to be inserted into the top of the disinfecting tube (11). The disinfecting tube (45) will hold a disinfecting solution (17). The device can formed with a small hole (14) in the bottom panel (23) to insure that the disinfecting tubes (45) will remain straight in the device. The disinfecting tubes (45) will optionally be removable by grabbing and lifting up on the top of the tube (11) through the top panel holes (33) to ensure easy cleaning of the device, and easy filling of the disinfecting solution (17). The disinfecting tube top (11) may be formed with a lip (13), to allow the user to easily remove the disinfecting tube (45) from the top panel (21) The disinfecting tube (45) may be formed with screw threads (18) so that a cap (15) can be used to cover the disinfecting solution (17) when not in use. The bottom panel (23) may be formed with base feet (3).

SUMMARY, RAMIFICATIONS, AND SCOPE

Accordingly, the reader can easily see that the scissor disinfesting device is a useful and practical device for the hair cutting stylist. This device is specifically designed to disinfect scissors on an individual basis. This device will ensure that the blades of the scissor are individually protected from foreign objects that may easily damage the razor sharp blades. This invention keeps the blades together during the disinfecting process to insure that a person will not accidentally cut themselves when attempting to access the scissors. This device is designed to use only the necessary amount of disinfecting solution for each needed scissor and insures that no solution will unnecessarily be used as is true in the devices cited in the prior art as a disinfecting jar or tray. This device offers many health advantages. By its use, scissors can easily and practicality be disinfected after each hair cut.

This device is practical because of its small compact size. It will fit on the often cluttered counters of hair stylists. It is an inexpensive device to manufacture and persons with common knowledge of plastics will easily be able to manufacture the invention. This invention offers a practical remedy for the disinfecting scissors which other devices have tried to complicate and make unpractical.

Although the description of this device may contain specifications, these should not be construed as limiting the scope of this invention but merely providing illustrations of the present invention. Thus the scope of this invention should be determined by the appended claims and their legal equivalents, rather than by the examples given.

I claim:

1. A scissor disinfecting device, the device comprising:

a top panel, a bottom panel, a side panel, and a plurality of disinfecting tubes, said side panel connecting said top panel to said bottom panel, said top panel being substantially parallel to said bottom panel, said top panel and said bottom panel each being substantially perpendicular to said side panel, said top panel having a plurality of holes, each of said plurality of holes defining means for holding one of said plurality of disinfecting tubes upright and vertically, each of said plurality of holes receiving one of said plurality of disinfecting tubes, each of said plurality of disinfecting tubes having an open top end and a closed bottom end, said closed bottom end of each of said plurality of disinfecting tubes resting on said bottom panel, the open top end of each of said plurality of disinfecting tubes extending beyond the upper surface of said top panel, each of said plurality of disinfecting tubes defining means for holding at least one pair of scissors upright and vertically and for permitting the handle of said at least one pair of scissors to extend beyond said open top end, each of said plurality of disinfecting tubes further defining means for containing a disinfecting solution and for disinfecting said at least one pair of scissors, whereby the handle of said at least one pair of scissors can be easily grabbed without touching the disinfecting solution.

* * * * *